United States Patent [19]

Burack et al.

[11] Patent Number: 5,105,876
[45] Date of Patent: Apr. 21, 1992

[54] MULTIPLE-UNIT PROBE PUSHER AND SYSTEM FOR DRIVING EDDY CURRENT INSPECTION PROBES IN THE HEAT EXCHANGER TUBES OF A NUCLEAR STEAM GENERATOR

[75] Inventors: Robert D. Burack, Pleasant Hills; William C. Ritz, Greensburg, both of Pa.; Charles E. Lutz, Glendale, Calif.

[73] Assignee: Westinghouse Electric Corp., Pittsburgh, Pa.

[21] Appl. No.: 375,989

[22] Filed: Jul. 6, 1989

[51] Int. Cl.⁵ ............... F28F 11/00; G21C 17/00
[52] U.S. Cl. ................... 165/11.2; 165/76; 242/54 R; 376/245; 376/260; 73/866.5; 73/865.8; 901/1; 901/44
[58] Field of Search ........... 165/11.2, 76; 242/54 R; 254/134.3; 376/245, 260; 73/866.5, 865.8; 901/1, 44

[56] References Cited

U.S. PATENT DOCUMENTS

| | | |
|---|---|---|
| 3,761,550 | 9/1973 | Seefluth . |
| 4,046,632 | 9/1977 | Puchelt et al. ............ 376/245 |
| 4,172,492 | 10/1979 | Abell et al. ............ 165/11.2 |
| 4,253,914 | 3/1981 | Fogelberg ............ 376/260 |
| 4,507,082 | 3/1985 | Wardlaw, III . |
| 4,580,052 | 4/1986 | Hoffman et al. ............ 376/245 |
| 4,757,258 | 7/1988 | Kelly, Jr. et al. . |
| 4,793,044 | 12/1988 | Cartry et al. ............ 376/260 |
| 4,802,379 | 2/1989 | Edajima ............ 376/245 |
| 5,000,681 | 3/1991 | Zafred et al. ............ 432/224 |

Primary Examiner—John K. Ford

[57] ABSTRACT

Disclosed is a system for driving inspection probes through steam generator tubes of a nuclear power plant, particularly eddy current probes. The system utilizes a single conduit that is connectable to the tube sheet of a steam generator and comprises a multiple-unit probe pusher having a housing containing a plurality of independently actuable drive paths, a multiple-unit probe storage device including a plurality of independently movable take-up reels, and a guide or deflector device for directing any one probe that is driven from any one of the drive paths of the probe pusher to the single conduit. Preferably, the entire system is also remotely controllable. The system enables one probe to be in use for tube inspection while providing readily available spare probes to replace a defective probe with a minimum of downtime and worker radiation exposure.

29 Claims, 6 Drawing Sheets

MULTIPLE-UNIT PROBE PUSHER AND SYSTEM FOR DRIVING EDDY CURRENT INSPECTION PROBES IN THE HEAT EXCHANGER TUBES OF A NUCLEAR STEAM GENERATOR

BACKGROUND OF THE INVENTION

This invention is generally related to a system for inspecting the heat exchanger tubes of a steam generator, and is specifically concerned with a multiple-unit probe pusher which can drive any one of a plurality of probes independently from one another and can reliably guide any one of the driven probes to a selected heat exchanger tube.

Probe pushers have seen extensive use in steam generator service applications. One application for probe pushers has been in the eddy current inspection of the steam generator heat exchanger tubing, which checks for faults or failures in the tubes. In eddy current inspection processes, the probe pusher is mounted outside of the steam generator so as to drive an eddy current probe through each tube to be inspected. During this operation, the steam generator and nuclear reactor are shutdown, and many hundreds of heat exchanger tubes are inspected. These eddy current probes have a limited useful life, and when an inspection probe fails, the inspection process must be stopped and a platform worker will have to be sent into the containment area to replace the defective probe. Currently-used eddy current probe pushers include means to drive a single eddy current probe through a steam generator heat exchange tube; but when failure of the probe occurs, a worker must remove the inspecting probe from the probe pusher and replace it with a new probe before the inspection operation can continue. These single drive probe pushers include a split housing that must be opened by the worker to remove and insert the inspection probes, which in turn increases service time, generator downtime (which typically costs the utilies over $600,000 per day in lost revenues) and radiation exposure to maintenance personnel. This is a significant disadvantage, particularly when one considers the fact that over three thousand tubes must typically be inspected in a single, walk-along maintenance operation, and that one or more inspection probes usually fail in each eight-hour shift.

In a different application of probe pushers in a steam generator of a nuclear reactor plant, it has been known to use a multiple-unit probe pusher as a positioning device for inserting and removing a plurality of heat treat stress relief probes all at once in a like multiple number of steam generator tubes for stress relief treatment. Such stress relief heater probes are fundamentally different from inspection probes such as eddy current probes because once the heater probes are positioned by the probe pusher next to the point on the tube to be treated, they, remain in place during the treatment of the tube. Hence the probe pusher is used only as a positioning device prior to the treatment of the tube. In contradistinction, eddy current probes must be driven along the longitudinal axis of the tube while the inspection operation is conducted, and the speed of inspection is directly related to the speed the probe is moved through the steam generator tubes.

The aforementioned probe pusher for positioning a multiple number of heater probes is designed to speed up the process of treating a large number of tubes of a steam generator by actually treating as many tubes with as many heater probes that the probe pusher can position in the tubes at the same time. Thus, stress relief treatment is expedited by treating many tubes in parallel at once. In order to accomplish the above, this known probe pusher includes a plurality of drive paths defined within a probe pusher housing, wherein each path includes a system of drive rollers and clutches between an inlet and an outlet of the housing for each of the heater probes to follow through. The clutches and rollers are mounted on shafts driven by a single drive shaft and the clutches are independently actuable so that each drive path can be operated independently to position heater probes.

While this prior art multiple-unit probe pusher is well adapted for use with heater probes, it is not well adapted for use with inspection probes. For example, upon the failure of any one of the probes being manipulated within a tube there is no simple way to replace the probe that becomes defective in operation without interrupting the operation of all of the probes, as all the probes are connected to flexible cables that are wound and unwound from a single drum. Additionally, this prior art probe pusher is not designed to quickly move its probes along the longitudinal axis of the tubes being treated. Instead, it moves its respective probes at a relatively slow speed since the purpose of such longitudinal movement is only to position the heater probes adjacent to a desired region of the tubes which require heat treatment.

Clearly, there is a need for a multiple probe pusher device and system that affords rapid replacement of defective probes with little or no interruption in the operation of the other probes, and which is capable of rapidly positioning the probes in the tubes and quickly moving them along the length of these tubes. Such a device would overcome the aforementioned shortcomings of increased downtime and radiation exposure while being able to adequately perform an inspection process such as eddy current inspection.

SUMMARY OF THE INVENTION

Generally speaking, the invention is a system driving inspection probes through heat exchanger tubes of a such as eddy current probes, by way of a single conduit connectable to the tube sheet area of the steam generator. The system comprises a multiple-unit probe pusher having a housing containing a plurality of independently actuable drive paths, wherein each path includes an inlet, an outlet and a plurality of drive wheels; a multiple-unit probe storage device including a plurality of probe take-up reels, wherein one take-up reel is associated with each drive path; a guide means for directing any one of the plurality of probes from the drive paths from the multiple-unit probe pusher to the single conduit; and a control system for independently actuating each of the drive paths as needed.

The multiple-unit probe pusher preferably includes four positively driven wheel shafts which are operatively connected with a single drive shaft driven from a motor outside the housing, and electromagnetic clutches connecting the drive wheels to the wheel shafts. These electromagnetic clutches can be controlled from an electrical source outside and remote from the probe pusher housing to selectively actuate and thereby lock the drive wheels to the wheel shafts. In the preferred embodiment, the wheel shafts on one side of the probe pusher device within the housing are floatingly and adjustably connected to the housing so that the drive system can compensate for some degree of difference in inspection probe diameters. Moreover, the drive wheels themselves are made of urethane of a somewhat resilient nature as a secondary feature enabling for compensation of different probe diameters.

Each of the takeup reels of the probe storage device is associated with one of the drive paths of the probe pusher, and the takeup reels are provided on the inlet side of the probe pusher so that an inspection probe taken from each reel can be fed into the probe pusher and driven out of the probe pusher. The takeup reel for each probe is independently moveable with respect to the other reels so that only one probe can be driven at a time. Each takeup reel can be freely rotatable so that the probe pusher simply unwinds a probe from the reel as needed or can be driven in accordance with the probe pusher drive mechanism at a corresponding angular speed.

The guide device in the preferred embodiment includes a deflector mechanism, such as a funnel shaped device, which can direct any one of the plural driven inspection probes from the probe pusher into a single conduit that is further connected to the tube sheet of the steam generator. Preferably, the guide device is connected with the probe pusher unit and has a wide enough opening for any one of the driven inspection probes to enter with tapered side walls directing any of the driven probes to the single conduit. Alternatively, a single conduit guide mechanism can be utilized with an opening at least sufficient for one probe to enter into the conduit that is adjustably moveable with respect to the probe pusher so that any one of the multiple probe drive path positions can be selected. Preferably, the selection process would also be done from a remote location.

The control system of the present invention will advantageously include a remote control panel that is connected via electrical cables to the drive motor, clutches, reels and guide mechanism of the present invention. Thus, it is not necessary to have a worker on the platform located near the manway of a steam generator, thereby permitting an operator from above to control all of the actions of the system.

When one of the inspection probes fails, such as an eddy current probe, the operator need not be present on the manway platform to feed a new eddy current probe in the probe pusher, but instead can remotely remove the defective probe and thereafter drive a new inspection probe that is one of the spares previously loaded in the probe pusher. Such a system advantageously saves worker time and worker exposure within the radiation area of the steam generator. The total time needed to do the entire inspection job can be reduced in that practically no time is lost when it becomes necessary to replace the inspection probe.

Preferably, the system of the present invention utilizes a three-unit probe pusher with a three wind up reel device and a guide device that can direct any one of the three probes driven from the probe pusher into a single conduit. Thus, it is apparent that even if one inspection probe fails each shift in a day, it is unnecessary to replace the probes but once every three or so shifts. Clearly, the amount of time cut down is considerable. And since it is fairly easy to load the inspection probes into the probe pusher of the present invention by simply inserting one end of each probe into the inlet of each drive path, of the probe pusher and thereafter selectively actuating each drive mechanism, it is apparent that worker exposure time is minimized as well as the total associated replacement time. Faster inspection time coupled with lower exposure to contaminated areas provides significant advantages over any prior art inspection system known to date.

BRIEF DESCRIPTION OF THE SEVERAL FIGURES

DETAILED DESCRIPTION OF THE PREFERRED EMBODIMENTS

Figure 1:
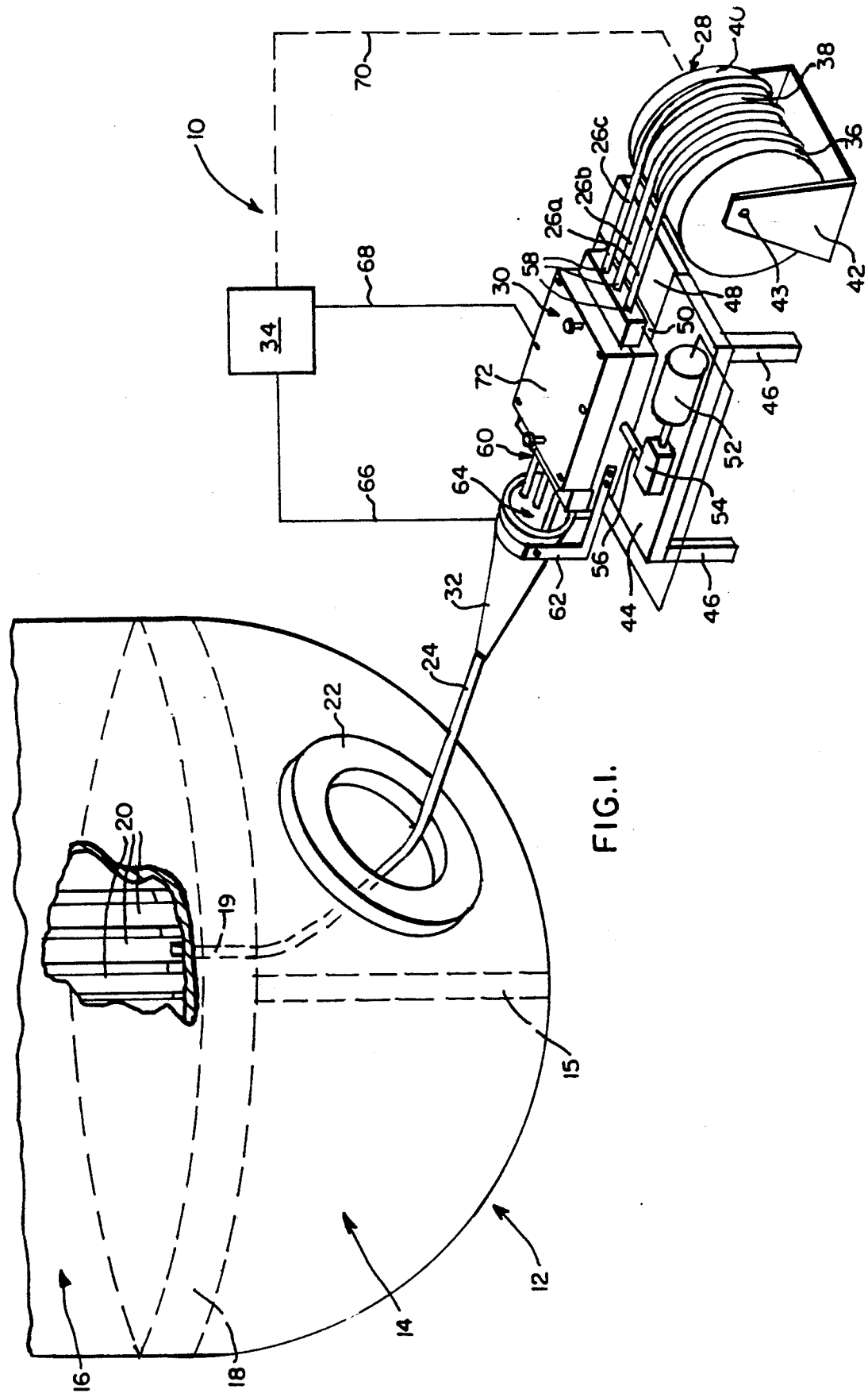
FIG. 1 is a schematic view of a system for driving inspection probes and a steam generator with parts of the system shown in perspective.

With reference now to the several figures and in particular to FIG. 1, wherein like components are designated by like reference numerals throughout all of the several figures. The system 10 of the invention is particularly adapted for driving inspection probes in a steam generator 12 of a nuclear power plant. Such steam generators 12 require normal maintenance operations periodically to inspect individual steam generator tubes 20 for possible areas of weakness or corrosion so as to prevent leakage of radioactive water.

The basic operation of a steam generator is as follows. Initially, water is heated by a nuclear reaction within a reaction vessel (not shown) and the water is then circulated from the reactor core into the primary side 14 of the steam generator 12. The primary side 14 is divided by a separator 15 into two halves, and the two halves are connected by a number of U-shaped heat exchanger tubes 20 that pass through the secondary side 16 of the steam generator. The secondary side 16 contains nonradioactive water which absorbs the heat from the heat exchanger tubes 20 and the heated water of the primary side 14 so as to boil the water in the secondary side 16 making steam for power generation. In order to effectively seal the primary side 14 from the secondary side 16, a tube sheet 18 is provided bores 19 that conduct and are sealingly connected to each of the tubes 20 so that the radioactive water in the primary side 14 can circulate through the secondary side 16 without becoming radioactively contaiminated. The contaminated water is then recirculated from the primary side 14 back to the reactor core to be reused.

Periodically, the heat exchanger tubes 20 are inspected from the primary side 14 of the steam generator 12 to look for potential areas of weakening or corrosion.

In order to accomplish this, the nuclear reactor must be shut down and entrance made into the primary side 14 by way of a manway 22 which is normally closed by a man door (not shown). In a typical steam generator 12, as many as 3,000 or more heat exchanger tubes must be inspected during a single period of down time for the reactor. Thus, it is of importance to inspect each of the tubes thoroughly and as quickly as possible to minimize down time and worker exposure at the contaminated side of the steam generator 12. A system for driving inspection probes in accordance with the above goals is shown at 10 and described as follows.

Initially, the system 10 is connected with a particular heat exchanger tube 20 by way of a conduit 24 that can be secured to any one of the openings 19 provided in the tube sheet 18. There are many known robotic tools in use at present for securing the conduit 24 to the tube sheet 18 at any one of the openings 19 therein. The structure and manner which such a robotic tool operates is not a part of the present invention. Suffice it to say that such tools are available.

Any one of inspection probes 26a, b, or c can be guided by conduit 24 into the appropriate heat exchange tube 20 for inspection. The inspection probes 26a, b, and c are stored, driven and guided by the system 10 of the present invention including in succession a multiple-unit probe storage apparatus 28, a multiple-unit probe pusher 30, and a guide or deflector device 32. Moreover, a control means 34 is provided to selectively operate the multiple-unit probe pusher system as will be more apparent below.

The multiple-unit probe storage apparatus is made up of individual take-up reels, of which three are shown at 36, 38, and 40, in association with the three probes 26a, b, and c. It is understood that the number of take-up reels should be at least as many as the number of probes that can be handled by the multiple-unit probe pusher 30, wherein three is shown as a preferred embodiment of the present invention. The take-up reels 36, 38, and 40 are supported by any conventional support means such as a stand as at 42, wherein the reels are rotatably mounted about a pivot access 43. Moreover, the take-up reels 36, 38, and 40 are rotatable independent of one another and may be freely rotatable about pivot access 43 or may include separate conventional drive motors for each take-up reel. If separate drive motors are used or a single motor with an independent clutching system, then it is necessary to time the angular speed of the take-up reels with the speed of the multiple-unit probe pusher 30 as will be more clear following the description of the multiple-unit probe pusher 30 below.

The multiple-unit probe pusher 30 is supported in any conventional manner so as to position the probe pusher 30 nearby or adjacent the manway 22 of the steam generator 12. This can be done by mounting a platform directly to the manway 22 or by providing a platform as shown at 44 supported by legs 46. It is also contemplated that the platform 44 could be suspended from above. Further and in cooperation between the probe pusher 30 and the platform 44 is a slide mechanism allowing the probe pusher 30 to move relative to the platform 44 by way of a key slot 48 in the upper surface of platform 44 and a key depending from the probe pusher 30. The key 50 is more clearly illustrated in FIGS. 3 and 4. Also provided with the probe pusher 30 is a drive motor 52 with gear box 54 which are responsible for driving shaft 56 at an appropriate speed to move the probes 26a, b and c at speed necessary for proper inspection. As can further be seen in FIG. 1, the probes 26a, b and c enter the probe pusher 30 at inlets 58, (of which there are preferrably three) and exit the probe pusher 30 at outlets 60 similarly provided on the opposite side of the probe pusher 30. The interior mechanisms of the drive devices of the probe pusher 30 will be described in greater detail below.

The guide or deflector device 32 is secured to the probe pusher 30 by way of L-shaped brackets 62 to hold the guide device 32 nearby the outlet 60 of the probe pusher 30. The guide device illustrated in FIG. 1 is basically a funnel shaped element that has an opening at 64 which is sufficiently wide to accommodate all three of the probes 26a, b and c therein. However, the side walls of the guide device 32 funnel inwardly to a point at an approximately similar diameter as the conduit 24, which is large enough to accommodate a single inspection probe 26a, b or c to be directed to the tube sheet 18. Thus, the system accommodates only one inspection probe 26a, b or c within the conduit 24 while the guide device 32 ensures that any one of the three probes 26a, b or c will be guided into the conduit 24. As also is evident from FIG. 1, two of the probes 26b and 26c are illustrated with their ends extending just into the opening 64 of the guide device 32. The other probe 26a is shown in an extended position, wherein the probe 26a can go as far as through the conduit 24 and completely through the heat exchange tube 20 to which the conduit 24 is connected. In operation, only one of the inspection probes is used at a time while the two others are maintained at the guide device 32 as spare probes which can be utilized for inspection (i.e. eddy current inspection) after the failure of the probe in use. Such operation provides a shorter overall inspection time with lower exposure of maintenance personnel to the radioactive environment of the generator.

The control means 34 is appropriately wired by way of electrical cables 66 and 68 to the motor 52 and the probe pusher 30 respectively. The reason for cable 68 will become apparent with the description of the interior drive mechanisms of the probe pusher 30 below. It is further contemplated to include another cable at 70 between the control means 34 and the first, second and third take-up reels 36, 38 and 40 respectively of the multiple-unit probe storage apparatus 28 so as to provide power to independently rotate any one of the take-up reels 36, 38 or 40 in conjunction with the activation of the probe pusher 30. However, as noted above, the take-up reels 36, 38 and 40 may simply be freely rotatable independently of one another.

The purpose of the control means 34 is to permit an operator to remotely operate all of the components of the system for driving the inspection probes from a safe position on a work platform above the steam generator 12. Thus, the control means 34 includes a remotely actuable switching and controlling mechanism, as are well known in the art of robotic control. This reduces the possible risks associated with radiation exposure by minimizing the amount of worker time at the radioactive primary side 14 of the steam generator 12. The control means 34 may also include cameras and monitors appropriately positioned so that an operator above can visually be aware of the operation of the entire system.

Figure 2:
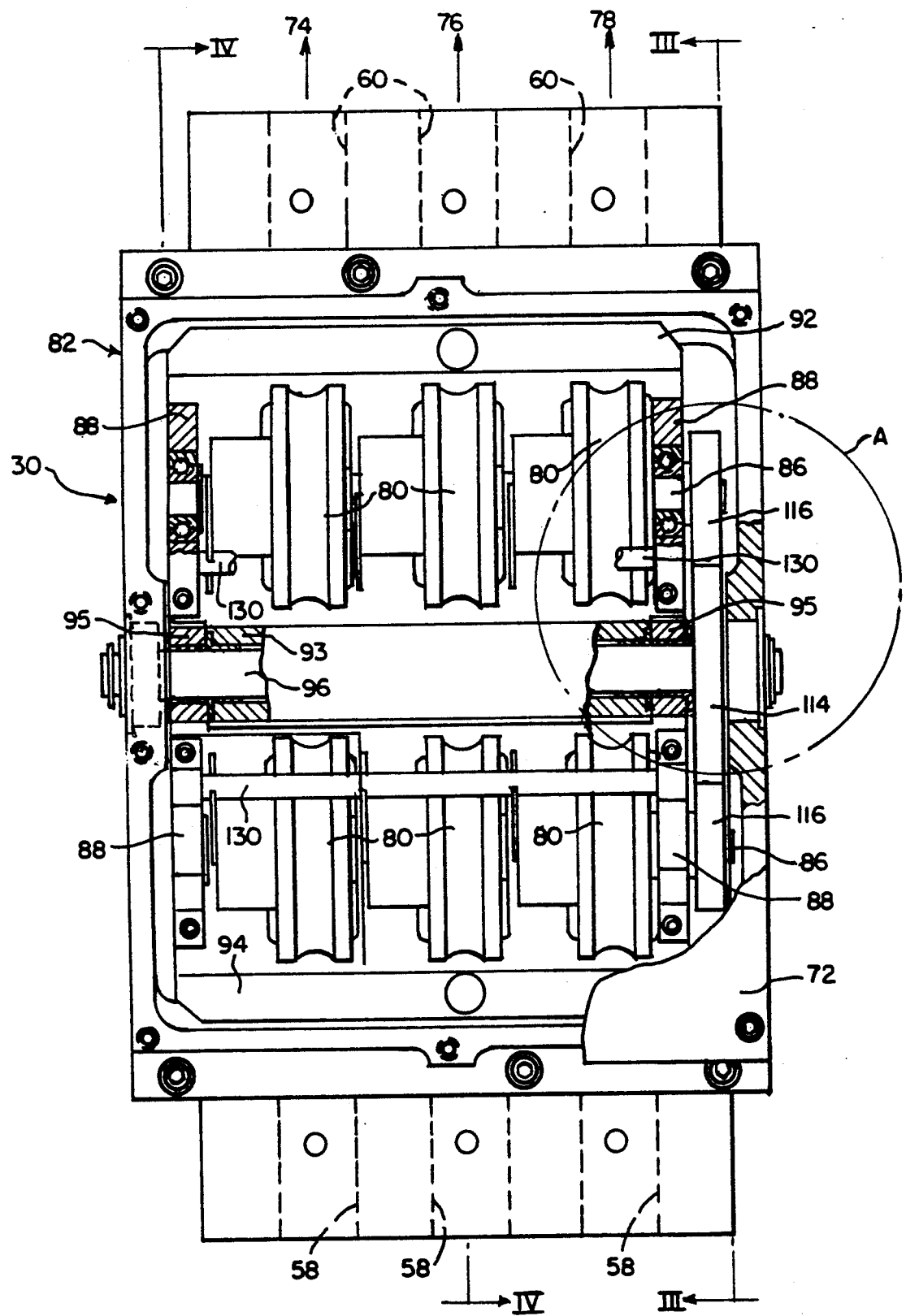
FIG. 2 is a top view of the probe pusher in accordance with the present invention partially in cross-section with the top cover removed.
Figure 3:
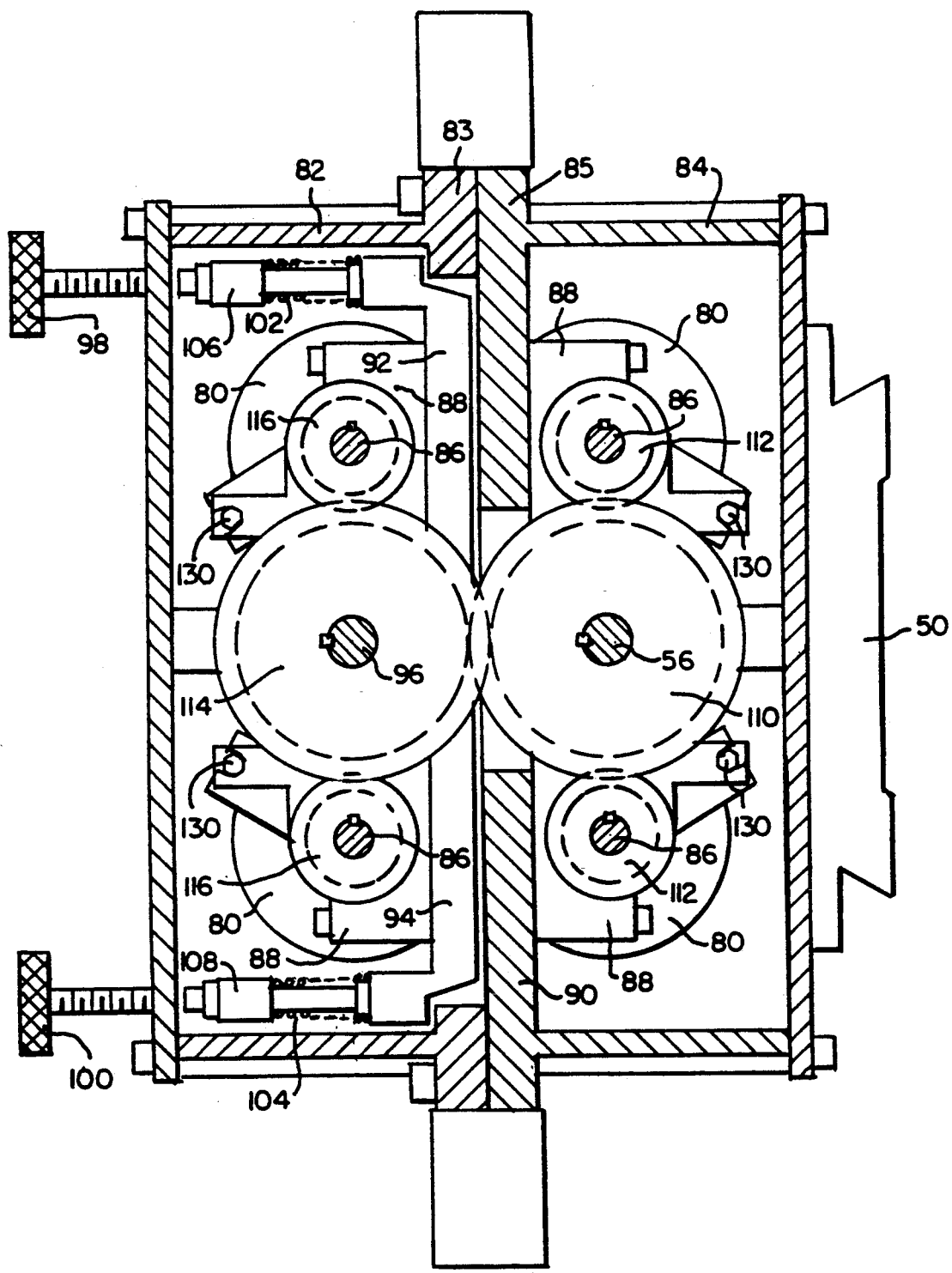
FIG. 3 is a cross-sectional view of the probe pusher in accordance with the present invention taken along line 3—3 of FIG. 2.

Now with reference to FIGS. 2-7, the particular details and interior mechanics of the probe pusher 30 will be described. FIG. 2 illustrates the probe pusher 30 with the top cover 72 removed except for a lower right corner portion. Three drive paths 74, 76 and 78 are shown in FIG. 2 corresponding to the preferred embodiment which drives three probes, wherein each drive path includes an inlet opening 58, a set of rollers 80, and an outlet opening 60. With reference now to FIG. 3 taken along line 3—3 of FIG. 2, it can be seen that the probe pusher 30 includes two housings 82 an 84 connected together at flanges 83 and 85 by way of conventional bolts or cap screws. Within the housing 82 and 84, the rollers 80 are supported on four driven shafts 86 by way of pillow blocks 88. The pillow blocks in the right hand side housing 84 of FIG. 3 are directly secured to a housing wall 90 so that these driven shafts 86 are rotatably supported within the housing 84. Note that conventional roller or ball bearings can be utilized between the pillow blocks 88 and the driven shafts 86 as shown and illustrated in FIG. 2.

Figure 7:
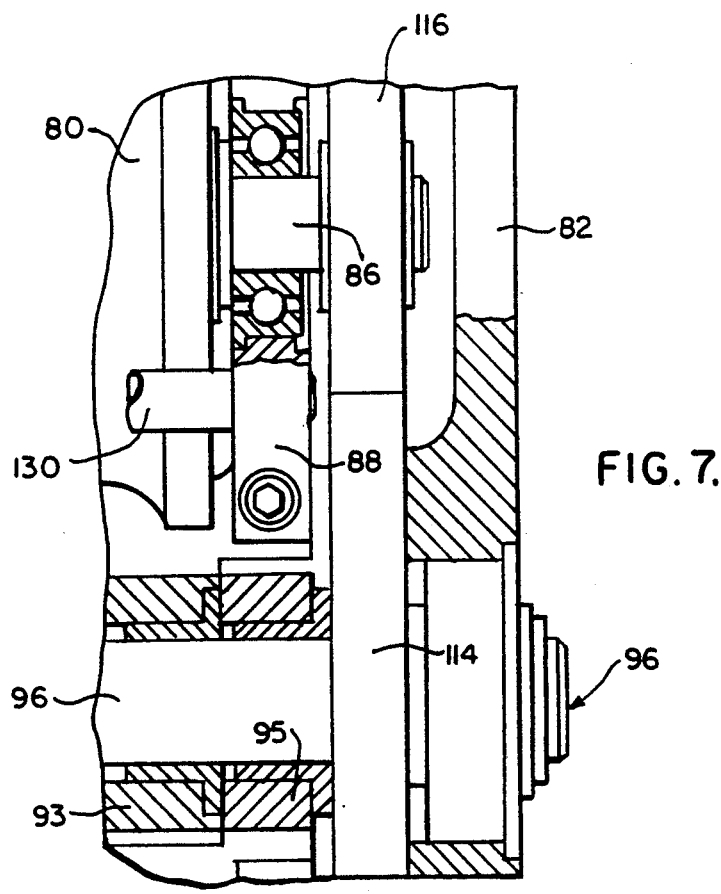
FIG. 7 is an enlarged view of the portion of FIG. 2 in circle A of the probe pusher in accordance with the present invention.

On the left side within housing 82, the pillow blocks 88 are not directly secured to any portion of the housing 82, but are movingly supported on brackets 92 and 94. The brackets 92 and 94 are pivotally supported on a idler shaft 96, see FIG. 2, the idler shaft 96 being supported by the side walls of the housing 82. Thereby, the upper bracket 92, as seen in FIG. 2 includes a rotable bearing portion 93 surrounding the idler shaft 96, and the lower bracket 94 includes two bearing portions 95 that also surround idler shaft 96 at positions axially outward of the bearing section 93. FIG. 7 shows a blow-up of the relevant area A of FIG. 2 illustrating bearing section 93 and 95 provided around idler shaft 96.

Since, the driven shafts 86 are mounted within housing 82 on the pillow blocks 88 by way of swingingly moveable brackets 92 and 94, the driven shafts 86 and thus the drive rollers 80 on those shafts 86 can be adjustably moved to or away from the relevant drive paths 74, 76 or 78 depending on the probe diameter of an inspection probe. This adjustment is further facilitated by thumbscrew 98 and 100 on brackets 92 and 94 respectively which can be controlled so as to vary a spring force or tension generated by springs 102 and 104 respectively, that position the driven shafts 86 and rollers 80 along the drive paths. By turning either of the thumbscrews 98 or 100, the tension in springs 102 and 104 can be adjusted as spring engagement portions 106 and 108 are moved to the right or to the left as viewed in FIG. 3. It is also contemplated that many other means to move the stop portions 106 and 108 and adjust the spring tension can be utilized such as stepper motors, solenoids, or hydraulic positioners. Such devices can be chosen so that they are more easily controlled from a remote location.

Referring again to FIG. 3, drive shaft 56, entering housing 84 from the gear box 54, is shown keyed to a drive gear 110. The drive gear 110 is in turn drivingly connected to driven gears 112 in a direct manner so as to drive the driven shafts 86 within side housing 84. Further, the drive gear 110 meshes and drives an idler 114 keyed to idler shaft 96 which in turn drives driven gears 116 keyed to driven shafts 86 within the side housing 82. Thus it can be seen that rotational drive provided at drive shaft 56 is transferred to drive each of the four driven shafts 86 either directly from drive gear 110 or indirectly through idler gear 114.

Since each of the driven shafts 86 are always operatively driven by the rotation of drive shaft 56, it is then necessary to selectively connect the drive rollers 80 to their respective driven shafts 86 so that selective sets of drive rollers 80 can be activated as the occasion demands. In other words, each drive roller 80 must be selectively connectable to its driven shaft 86 so that the roller can be driven by the shaft 86 or rotatable thereto in a non-driving mode.

Figure 6:
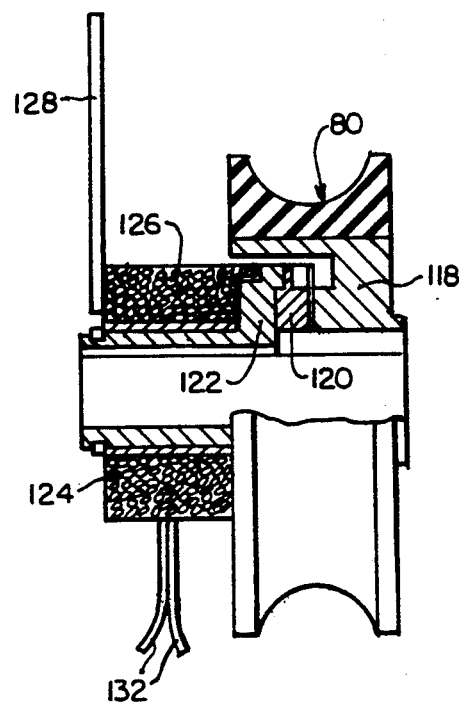
FIG. 6 is a partial cross-sectional view illustrating the electromagnetic clutch mechanism used in the probe pusher of the present invention.

In order to accomplish the selectable drive connection an electromagnetic clutch device is provided between each drive roller 80 and its respective driven shaft 86. Such electromagnetic clutches are conventional and known in the art and can be purchased from American Precision Industries, Deltran Division, Part No. CS11-24-6-6 in Buffalo, N.Y. This basic electromagnetic clutch is modified as shown in FIG. 6 for adaption to the present invention. The roller 80 is freely rotatably supported on any one of the driven shafts 86 by way of a hub 118. This hub 118 is preferrably made of aluminum. Also rotatably secured with the hub 118 is a rotor 120, also freely rotatably disposed around shaft 86. Keyed to the shaft 86 for constant drive transfer is an armature 122 surrounded by a rotatable bushing 124 that acts as a cup to hold field coil windings 126. Connected to the bushing 124 is an antirotation tab 128 which is further fixed in position by a rod 130 nonmovably supported in pillow blocks 88. By this construction, the field coils 126 are prevented from rotation and are maintained in position about the armatures 122, are rotated with the driven shafts 86. Then, to drivingly connect a driven shaft 86 and keyed armature 122 to the wheel hub 118, one must simply energize the field coil windings 126 causing the rotor 120 to lock with the armature 122 and thus drive roller 80. In this way, selective energizing of the electromagnetic clutches results in the selective energizing of drive paths 74, 76 or 78. Each drive path consisting of four driven rollers 80.

In operation of the probe pusher unit 30, one must energize the four clutches of the four rollers 80 associated with each drive paths 74, 76 or 78 selectively to activate one such drive path. Power is provided to each of the field coil windings 126 by way of electrical leads 132, shown in FIG. 6, which are run to connect with the cable 68 to the control means 34 for remote operation of each electromagnetic clutch.

Additionally to accommodate slight differences in diameters of inspection probes fed through the probe pusher 30, the rollers 80 are formed of a resilient material such as urethane of sufficient thickness. See FIG. 6 where the resilient portion of the rollers 80 are provided radially ouward of the hub 118.

Figure 4:
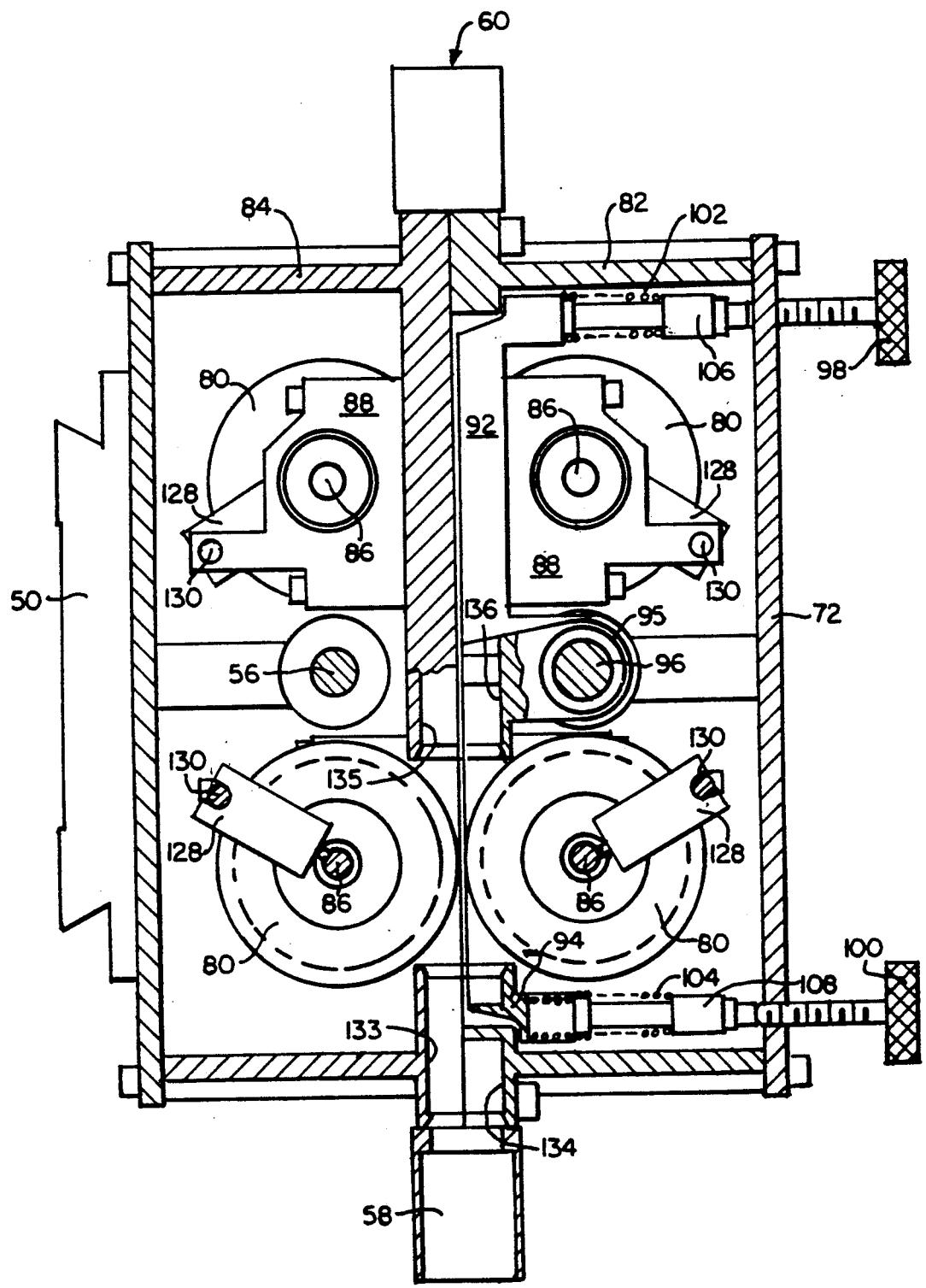
FIG. 4 is another cross-sectional view of the probe pusher in accordance with the present invention taken along line 4—4 of FIG. 2.
Figure 5:
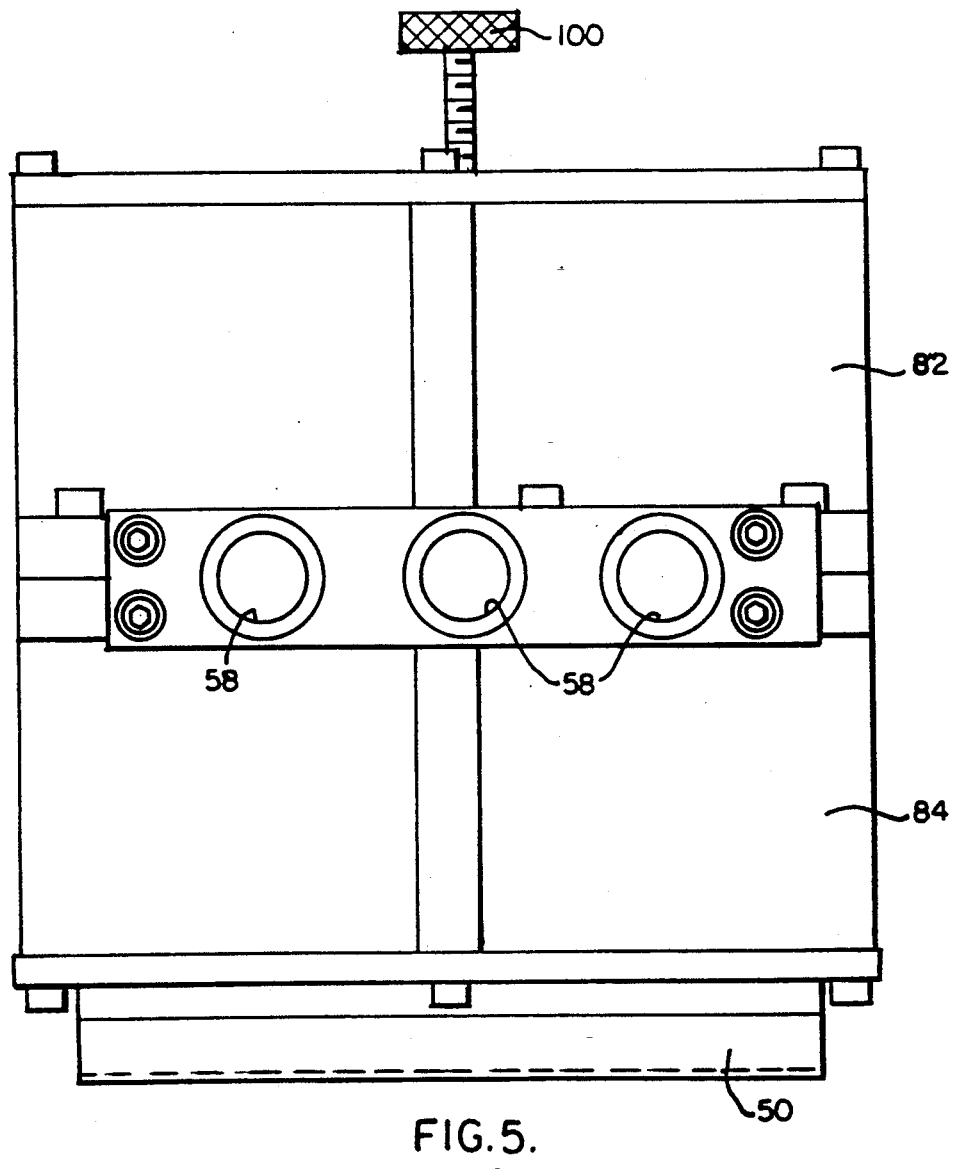
FIG. 5 is an end view of the probe pusher in accordance with the present invention.

Referring now to FIGS. 4 and 5, it can be seen how a probe will enter any one of inlets 58, will be guided by cooperating channels 133, 134, 135 and 136 formed within the housings 82 and 84 so as to permit passage between two pairs of the rollers 80 and will be guided out through outlets 60. Note that the cooperating channels 133–136 include tapered edges for ease of guiding the probe through one of the drive paths. It is also noted in FIG. 4 that by way of the moveable rollers 80, on the right side of FIG. 4, allowing the shafts 86 to pivot about the idler shaft 96, varying degrees of diameters of probes can pass through the nip between rollers 80 up to the diameter of the opening formed by the cooperating channels 133–136 in the housings. Moreover, the resilient wheels provide an additional compensation.

Figure 8:
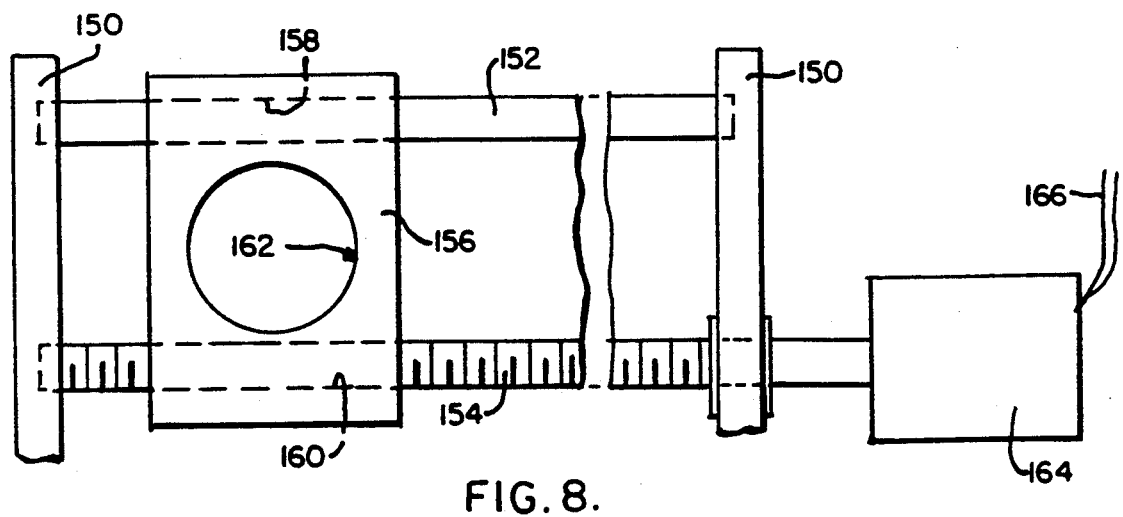
FIG. 8 is a side view of an alternate guide device to be used in the system according to the present invention.

Referring now to FIG. 8, a second embodiment for a guide means for directing any one of the inspection probes driven from any one of the drive paths 74, 76 or 78 is illustrated. In this embodiment, brackets 150 are mounted to the probe pusher 30 in a like manner as the brackets 62 of the funnel type guide means 32. However, extending between the brackets 150 is a guide rod 152 and an axially fixed but rotatable threaded shaft 154. The threaded shaft 154 is axially fixed in any known manner such as including thrust bearings at the brackets 150. A sliding block 156 including a slide bore 158 and a threaded bore 160 is mounted on the guide rod 152 and threaded shaft 154 as shown. Through the center of the sliding block is an opening 162 adapted to secure a conduit therein such as the conduit 24 shown in FIG. 1. The conduit 24 can be retained in the opening 162 by friction or any other conventional clamp means. Furthermore, a stepper motor 164 is drivingly connected to the threaded shaft so that upon the energizing of the stepper motor 164, the threaded shaft 154 is driven and the slide block 156 is moved accordingly. By using a stepper motor and encoder, it is possible to accurately and quickly align the opening 162 and conduit 24 in front of any one of the plurality of drive paths. Thus, a probe driven through any one of the drive paths can be accurately and reliably directed to the steam generator for the inspection process. Likewise, the stepper motor is connected via lead cables 166 to the control means 34 for remote operation. It is also understood that many other similar guide means could be obviously utilized to simply position a single conduit opening in front of any one of a plurality of drive paths. Other devices could utilize solenoids, mechanical linkages, or hydraulics.

We claim:

1. A system for driving inspection probes through heat exchanger tubes in a nuclear steam generator, said system comprising:
   a) a multiple-unit probe pusher including a housing containing a plurality of independently actuable drive means and a same plurality of inlets and outlets passing through said housing, thereby providing a plurality of probe drive paths, each having an inlet, an outlet, and a drive means;
   b) a control means for independently actuating each of said plurality of drive means of said multiple-unit probe pusher;
   c) a multiple-unit probe storage means located outside of the nuclear steam generator including a plurality of probe take-up means for feeding and receiving a probe to and from said multiple-unit probe pusher, wherein there is at least one take-up means for each probe drive path; and
   d) a guide means for receiving and directing selected probes from any one of said plurality of probe drive paths from said multiple-unit probe pusher to selected tubes for inspection,
   wherein said guide means is incapable of receiving all of said probes simultaneously such that at least one of said probes and its associated drive path is immediately available as a spare in the event that one of the selected probes fails.

2. The system of claim 1, wherein said plurality of probe take-up means are each operable independently of each other.

3. The system of claim 2, wherein each probe take-up means comprises a reel rotatably mounted on a common axis.

4. The system of claim 2, wherein each probe take-up means comprises a reel rotatably mounted on a common axis, and each reel is independently driven by a motor means that is operatively connected with said control means so as to actuate one of said motor means concurrently with the associated drive means of each probe drive path.

5. The system of claim 2, including a drive shaft and at least two driven shafts rotatably mounted in said housing, wherein said driven shafts are positively driven from said drive shaft by transfer means, and each of said driven shafts is provided with drive rollers of a same number as there are drive paths, and rollers being selectively connected to said driven shafts by clutch means.

6. The system of claim 5, wherein said inlets and said outlets are colinearly provided through said housing and at least one driven shaft is disposed on each side of a plane passing through said inlets and said outlets.

7. The system of claim 6, wherein each of said plurality of drive means comprises one roller on each driven shaft that is positioned in line with the inlet and outlet of each drive path, thereby making a set of rollers for each drive path.

8. The system of claim 7, wherein said control means is electrically connected to each clutch means so that upon energization of the clutch means, the roller is drivingly engaged to said driven shaft, whereby each set of rollers can be concurrently engaged to the driven shafts independently of other sets of rollers to independently actuate each drive means of each probe drive path.

9. The system of claim 8, wherein there are four driven shafts with two on each side of said plane, and there are three rollers on each driven shaft corresponding to three drive paths.

10. The system of claim 9, wherein the driven shafts on one side of said plane are adjustably connected to said housing by bias means so that a nip between rollers of one set of rollers can be varied.

11. The system of claim 10, wherein said bias means comprises a swinging bracket pivotally mounted about an idler shaft, said swinging bracket rotatably supporting one driven shaft and its associated rollers, and an adjustable tension spring means between said swinging bracket and said housing.

12. The system of claim 11, wherein said transfer means includes a drive gear fixed with said drive shaft, an idler gear fixed with said idler shaft and in drive engagement with said drive gear, and driven gears fixed to each driven shaft with two driven gears in engagement with said idler gear and two driven gears in engagement with said drive gear.

13. The system of claim 12, wherein said drive shaft extends out of said housing and is driven by an external motor means, and said motor means is connected to said control means for selective actuation said motor means capable of driving said rollers at a speed sufficient to drive an inspection probe at its operational speed.

14. The system of claim 1, wherein said guide means is positioned adjacent said outlets of said multiple-unit probe pusher, said guide means comprising a funnel-like member having a first opening facing said outlets that is of sufficient size to receive a probe coming from of any one of the outlets, and deflector walls for directing any driven probe toward a second opening that is smaller than said first opening but sufficiently large to permit one probe to pass therethrough, said second opening being connected to said conduit.

15. The system of claim 1, wherein said guide means is positioned adjacent said outlets of said multiple-unit probe pusher, said guide means comprising a slider block with means for connection to said conduit, and slide means for movably positioning said conduit to receive a probe driven from any one of said outlets.

16. A system for driving eddy current inspection probes through heat exchanger tubes of a nuclear steam generator, said system comprising:
   a) a multiple-unit probe pusher including a housing containing a plurality of independently actuable drive means and a same plurality of inlets and outlets passing through said housing, thereby providing a plurality of probe drive paths, each comprising an inlet, an outlet and a drive means;
   b) a control mans for independently actuating each of said plurality of drive means of said multiple-unit probe pusher;
   c) a multiple-unit probe storage means located outside of the nuclear generator including a plurality of probe take-up means for feeding and receiving a probe to and from said multiple-unit probe pusher, wherein there is at least one take-up means for each probe drive path and each take-up means operates independently of the others; and
   d) a guide means positioned adjacent the outlets of said multiple-unit probe pusher for receiving and directing only one of said probes from said multiple-unit probe pusher to a single tube for inspection such that the other probes and their associated drive paths are immediately available as spares in the event that the selected probe fails.

17. The system of claim 16, wherein each probe take-up means comprises a reel rotatably mounted on a common axis, and each reel is freely rotatable on said common axis.

18. The system of claim 16, wherein each probe take-up means comprises a reel rotatably mounted on a common axis, and each reel is independently driven by a motor means that is operatively connected with said control means so as to actuate one of said motor means concurrently with the associated drive means of each probe drive path.

19. The system of claim 16, including a drive shaft and at least two driven shafts rotatably mounted in said housing, wherein said driven shafts are positively driven from said drive shaft by transfer means, and each of said driven shafts is provided with drive rollers of a same number as there are drive paths, and rollers being selectively connected to said driven shafts by clutch means.

20. The system of claim 19, wherein said inlets and said outlets are colinearly provided through said housing and at least one driven shaft is disposed on each side of a plane passing through said inlets and said outlets.

21. The system of claim 20, wherein each of said plurality of drive means comprises one roller on each driven shaft that is positioned in line with the inlet and outlet of each drive path, thereby making a set of rollers for each drive path.

22. The system of claim 21, wherein said control means is electrically connected to each clutch means so that upon energization of the clutch means, the roller is drivingly engaged to said driven shaft, whereby each set of rollers can be concurrently engaged to the driven shafts independently of other sets of rollers to independently actuate each drive means of each probe drive path.

23. The system of claim 22, wherein there are four driven shafts with two on each side of said plane, and there are three rollers on each driven shaft corresponding to three drive paths.

24. The system of claim 23, wherein the driven shafts on one side of said plane are adjustably connected to said housing by bias means so that a nip between rollers of one set of rollers can be varied.

25. The system of claim 24, wherein said bias means comprises a swinging bracket pivotally mounted about an idler shaft, said swinging bracket rotatably supporting one driven shaft and its associated rollers, and an adjustable tension spring means between said swinging bracket and said housing.

26. The system of claim 25, wherein said transfer means includes a drive gear fixed with said drive shaft, an idler gear fixed with said idler shaft and in drive engagement with said drive gear, and driven gears fixed to each driven shaft with two driven gears in engagement with said idler gear and two driven gears in engagement with said drive gear.

27. The system of claim 26, wherein said drive shaft extends out of said housing and is driven by an external motor means, and said motor means is connected to said control means for selective actuation said motor means capable of driving said rollers at a speed sufficient to drive an inspection probe at its operational speed.

28. The system of claim 16, wherein said guide means is positioned adjacent said outlets of said multiple-unit probe pusher, said guide means comprising a funnel-like member having a first opening facing said outlets that is of sufficient size to receive a probe coming from of any one of the outlets, and deflector walls for directing any driven probe toward a second opening that is smaller than said first opening but sufficiently large to permit one probe to pass therethrough, said second opening being connected to said conduit.

29. The system of claim 16, wherein said guide means is positioned adjacent said outlets of said multiple-unit probe pusher, said guide means comprising a slider block with means for connection to said conduit, and slide means for movably positioning said conduit to receive a probe driven from any of said outlets.

* * * * *